United States Patent
Zhang et al.

(10) Patent No.: US 9,827,544 B2
(45) Date of Patent: Nov. 28, 2017

(54) REACTION DEVICE FOR PREPARING LIGHT OLEFINS FROM METHANOL AND/OR DIMETHYL ETHER

(71) Applicant: DALIAN INSTITUTE OF CHEMICAL PHYSICS, CHINESE ACADEMY OF SCIENCES, Dalian (CN)

(72) Inventors: Tao Zhang, Dalian (CN); Mao Ye, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 71 days.

(21) Appl. No.: 15/039,471

(22) PCT Filed: Dec. 3, 2013

(86) PCT No.: PCT/CN2013/088413
§ 371 (c)(1),
(2) Date: May 26, 2016

(87) PCT Pub. No.: WO2015/081494
PCT Pub. Date: Jun. 11, 2015

(65) Prior Publication Data
US 2017/0001164 A1   Jan. 5, 2017

(51) Int. Cl.
*B01J 8/00* (2006.01)
*B01J 8/18* (2006.01)
(Continued)

(52) U.S. Cl.
CPC ............... *B01J 8/26* (2013.01); *B01J 8/1827* (2013.01); *B01J 8/1872* (2013.01); *B01J 8/34* (2013.01);
(Continued)

(58) Field of Classification Search
CPC ..... B01J 8/00; B01J 8/18; B01J 8/1818; B01J 8/1827; B01J 8/1836; B01J 8/1872;
(Continued)

(56) References Cited

U.S. PATENT DOCUMENTS

| | | | |
|---|---|---|---|
| 4,670,410 A * | 6/1987 | Baillie | B01J 8/0055 208/161 |
| 6,166,282 A | 12/2000 | Miller | |
| 2014/0310980 A1* | 10/2014 | Jacob | B01J 2/16 34/589 |

FOREIGN PATENT DOCUMENTS

| | | |
|---|---|---|
| CN | 102276404 A | 12/2011 |
| CN | 102276406 A | 12/2011 |

(Continued)

OTHER PUBLICATIONS

Abstract of CN 102464535 A.*

*Primary Examiner* — Natasha Young
(74) *Attorney, Agent, or Firm* — Enshan Hong; VLP Law Group LLP

(57) ABSTRACT

A reaction device for preparing light olefins from methanol and/or dimethyl ether, and more specifically relates to a reaction device for preparing light olefins from methanol and/or dimethyl ether, which mainly comprises a dense phase fluidized bed reactor (2), a cyclone separator (3), a stripper (5), a lift pipe (7), a dense phase fluidized bed regenerator (10), a cyclone separator (11), a stripper (13), and a lift pipe (15), wherein the dense phase fluidized bed reactor (2) is separated into n (n≥2) secondary reaction zones by a material flow controller (17), and the dense phase fluidized bed regenerator (10) is separated into m (m≥2) secondary regeneration zones by the material flow controller (17).

15 Claims, 5 Drawing Sheets

(51) Int. Cl.
    *B01J 8/24*         (2006.01)
    *B01J 8/26*         (2006.01)
    *B01J 8/34*         (2006.01)
    *C07C 1/00*        (2006.01)
    *C07C 1/20*        (2006.01)

(52) U.S. Cl.
    CPC ......... *C07C 1/20* (2013.01); *B01J 2208/0015* (2013.01); *B01J 2208/00902* (2013.01); *B01J 2208/00938* (2013.01); *Y02P 30/42* (2015.11)

(58) Field of Classification Search
    CPC ......... B01J 8/24; B01J 8/26; B01J 8/34; B01J 2208/00–2208/00017; B01J 2208/0106; B01J 2208/00115; B01J 2208/0015; B01J 2208/00796; B01J 2208/00893; B01J 2208/00902; B01J 2208/00938; C07C 1/00; C07C 1/20; Y02P 30/00; Y02P 30/40; Y02P 30/42
    See application file for complete search history.

(56) References Cited

FOREIGN PATENT DOCUMENTS

| | | | |
|---|---|---|---|
| CN | 102463074 A | | 5/2012 |
| CN | 102464535 A | * | 5/2012 |
| CN | 101402538 B | | 1/2013 |
| CN | 102875289 A | | 1/2013 |
| CN | 102875296 A | | 1/2013 |
| WO | WO 2012/152258 A1 | * | 11/2012 |

* cited by examiner

A-A section

C-C section

US 9,827,544 B2

REACTION DEVICE FOR PREPARING LIGHT OLEFINS FROM METHANOL AND/OR DIMETHYL ETHER

RELATED APPLICATIONS

This is a U.S. national stage of international application No. PCT/CN2013/088413, now WO 2015/081494, filed on Dec. 3, 2013.

FIELD OF THE INVENTION

This disclosure relates to a reaction device for preparing light olefins from methanol and/or dimethyl ether.

BACKGROUND OF THE INVENTION

Light olefins, which are ethylene and propylene, are two important kinds of basic chemical raw materials, and the demand thereof is increasing. Generally, ethylene and propylene are produced via a petroleum scheme. However, the costs for producing ethylene and propylene from petroleum resources are increasing due to limited supply and relatively high price of petroleum resources. In recent years, techniques for preparing ethylene and propylene by converting substituent raw materials have been greatly developed. More attentions have been paid to the process of methanol-to-olefins (MTO), and the production scale on an order of million tons has been achieved. As the world economy develops, the demand for light olefins, particularly propylene, is increasing. It is reported as the analysis of CMAI Corporation that the demand for ethylene will increase at an average rate of 4.3% per year and the demand for propylene will increase at an average rate of 4.4% per year before 2016. Due to high-speed increase of the economy in China, all of the annual increase rates of the demand for ethylene and propylene in China exceed the average level of the world.

In early 1980s, UCC Corporation successfully developed SAPO molecular sieves, wherein the SAPO-34 molecular sieve catalyst exhibits excellent catalytic performance when it is used in MTO reaction, and has very high selectivity for light olefins and very high activity. However, after the catalyst has been used for a period of time, the activity is lost due to carbon deposition. A remarkable induction period is present in the use of the SAPO-34 molecular sieve catalyst. In the induction period, the selectivity for olefins is relatively low and the selectivity for alkanes is relatively high. As the reaction time increases, the selectivity for light olefins gradually increases. After the induction period, the catalyst maintains high selectivity and high activity in a certain period of time. With the subsequent elongation of the time, the activity of the catalyst rapidly decreases.

U.S. Pat. No. 6,166,282 discloses a technique and a reactor for converting methanol to light olefins, which use a fast fluidized bed reactor, wherein after the completion of a reaction in a dense phase reaction zone having a relatively low gas speed, a gas phase rises to a fast separation zone having an inner diameter which rapidly becomes smaller, and most of the entrained catalyst is preliminarily separated using a special gas-solid separation apparatus. Since the product gas and the catalyst are rapidly separated after reaction, a secondary reaction is effectively prevented. Upon analog computation, the inner diameter of the fast fluidized bed reactor and the storage amount of the catalyst required are both greatly reduced, compared to the conventional bubbling fluidized bed reactors. However, the carbon based yields of light olefins in this method are all typically about 77%, and there problems concerning relatively low yields of light olefins.

CN101402538B discloses a method for increasing the yield of light olefins. This method provides a second reaction zone on the upper part of a first reaction zone for converting methanol to light olefins, and the diameter of the second reaction zone is greater than that of the first reaction zone to increase the residence time of the product gas from the outlet of the first reaction zone in the second reaction zone, such that the unreacted methanol, the generated dimethyl ether, and hydrocarbons having 4 or more carbons continue react so as to achieve the object of increasing the yield of light olefins. This method may increase the yield of light olefins to some extent. However, since the catalyst from the first reaction zone has already carried a lot of deposited carbon and relatively high catalyst activity is required to crack hydrocarbons having 4 or more carbons, the conversion efficiencies of hydrocarbons having 4 or more carbons in the second reaction zone in this method are still slightly low, such that the yield of light olefins is slightly low.

CN102276406A discloses a method for increasing the production of propylene. This technique provides three reaction zones, wherein a first rapid bed reaction zone is used for converting methanol to olefins, and a lift pipe reaction zone and a second rapid bed reaction zone are connected in series to convert ethylene, hydrocarbons having 4 or more carbons, and unreacted methanol or dimethyl ether. In this patent, the residence time of substances, such as hydrocarbons having 4 or more carbons, etc., in the reaction zone and the second rapid bed reaction zone is relatively short and the conversion efficiency is relatively low, such that the yield of propylene is slightly low.

CN102875289A discloses a fluidized bed reaction device with a lift pipe reactor arranged therein, which is used for increasing the yield of light olefins. A first raw material is passed into a fluidized bed reaction zone and is brought into contact with a catalyst to generate a product comprising light olefins, and at the meanwhile a spent catalyst is formed; a part of the spent catalyst is passed into a regenerator for regeneration to form a regenerated catalyst, and the other part of the spent catalyst is passed into a lift pipe with an outlet end located in the reaction zone and is brought into contact with a second raw material so as to lift the spent catalyst into the reaction zone; and the regenerated catalyst is returned to the reaction zone of the fluidized bed reactor. Since the reaction device disclosed in this patent does not comprises a stripping portion, the spent catalyst will be passed into the regenerator with carrying a part of the product gas and is combusted with oxygen to reduce the yield of light olefins.

The technique for preparing olefins from methanol disclosed in CN102875296A provides three reaction zones, which are a rapid bed, a downer, and a lift pipe. Since the catalyst is circulated among the regenerator, the rapid bed, the lift pipe, and the downer, the flow direction is extremely complex, the distribution and the control of the flow rate are extremely difficult, and the activity of catalyst greatly changes.

As well known in the art, the selectivity for light olefins is closely associated with the amount of carbon deposition on the catalyst. A certain amount of carbon deposition on SAPO-34 catalyst is needed to ensure a high selectivity for light olefins. Main reactors used in current MTO process are fluidized beds. The fluidized bed is close to a continuously stirred tank reactor, which has wide a distribution of carbon deposition on catalyst and is not advantageous for increasing the selectivity for light olefins. Since the catalyst-to-alcohol ratio is very small and the coke yield rate is relatively low in the MTO process, in order to achieve a lager and controllable catalyst circulation volume, it is required to control the amount of carbon deposition and the uniformity of carbon content on the catalyst in the regeneration zone to certain levels. Therefore, the object of controlling the amount of carbon deposition and the uniformity of carbon content on the catalyst in the reaction zone is achieved. Therefore, it is a key technique in the MTO process to control the amount of carbon deposition and the uniformity of carbon content of the catalyst in the reaction zone to certain levels.

In order to solve the problems described above, a few researchers propose the techniques, such as providing an upper and a lower reaction zones in a fluidized bed, two fluidized beds connected in series, and a fluidized bed, a lift pipe, and a downer connected in series, etc. These preliminarily disclose methods for controlling the amount of carbon deposition and the uniformity of carbon content of the catalyst, and certain advantageous effects have been obtained. However, the complexity and the controlling difficulty of the MTO process are increased at the meanwhile. This disclosure proposes a solution of forming a plurality of secondary reaction zones (regeneration zones) by providing inner members in a dense phase fluidized bed to solve the problems of controlling the amount of carbon deposition and the uniformity of carbon content of the catalyst so as to increase the selectivity of light olefins.

SUMMARY OF THE INVENTION

The technical problem to be solved by this disclosure is the problem that the selectivity for light olefins in the prior art is not high present, and provides a new reaction device with the selectivity of light olefins increased. This reaction device is used in the production of light olefins, and has the advantages of good carbon deposition uniformity of catalyst, relatively high yield of light olefins, and good economical efficiency of the production process of light olefins.

In order to solve the problems described above, this disclosure provides a reaction device for preparing light olefins from methanol and/or dimethyl ether, comprising a dense phase fluidized bed reactor (2), a cyclone separator (3), a stripper (5), a lift pipe (7), a dense phase fluidized bed regenerator (10), a cyclone separator (11), a stripper (13), and a lift pipe (15); wherein a feeding line for reactor (1) is connected to the bottom of the dense phase fluidized bed reactor (2); a part of the stripper (5) is in the dense phase fluidized bed reactor (2), and the remaining part thereof is below the dense phase fluidized bed reactor (2); the bottom of the lift pipe (7) is connected to the bottom of the stripper (5), and the top of the lift pipe (7) is connected to the dense phase fluidized bed regenerator (10); a feeding line for regenerator (9) is connected to the bottom of the dense phase fluidized bed regenerator (10); a part of the stripper (13) is in the dense phase fluidized bed regenerator (10), and the remaining part thereof is below the dense phase fluidized bed regenerator (10); the bottom of the lift pipe (15) is connected to the bottom of the stripper (13), and the top of the lift pipe (15) is connected to the dense phase fluidized bed reactor (2), characterized in that a material flow controller (17) is provided in the dense phase fluidized bed reactor (2) and/or the dense phase fluidized bed regenerator (10), and the dense phase fluidized bed reactor (2) is separated into n secondary reaction zones by the material flow controller (17) and the $1^{st}$ to the $n^{th}$ secondary reaction zones are sequentially connected; the dense phase fluidized bed regenerator (10) is separated into in secondary regeneration zones by the material flow controller (17) and the $1^{st}$ to the $m^{th}$ secondary regeneration zones are sequentially connected; and wherein n≥2, and m≥2.

In one preferred embodiment, the top of the lift pipe (15) is connected to the $1^{st}$ secondary reaction zone, the $n^{th}$ secondary reaction zone is connected to a material overflow port (18) on the upper part of the stripper (5); and the cyclone separator (3) is provided on the upper part of the dense phase fluidized bed reactor (2), a top outlet of the cyclone separator (3) is connected to a product material line (4), and the bottom of the cyclone separator (3) is connected to the $n^{th}$ secondary reaction zone.

In one preferred embodiment, the top of the lift pipe (7) is connected to the $1^{st}$ secondary regeneration zone, the $m^{th}$ secondary regeneration zone is connected to a material overflow port (18) on the upper part of the stripper (13); and the cyclone separator (11) is provided on the upper part of the dense phase fluidized bed regenerator (10), a top outlet of the cyclone separator (11) is connected to an exhaust gas line (12), and the bottom of the cyclone separator (11) is connected to the $m^{th}$ secondary regeneration zone.

In one preferred embodiment, 8≥n≥3.

In one preferred embodiment, 8≥m≥3.

In one preferred embodiment, the material flow controller (17) is composed of a partition plate (19), an orifice (20), a material downward flow pipe (21), a bottom baffle (22), and a heat extraction member (23); and the orifice (20) is located below the partition plate (19) and is connected to the bottom of the material downward flow pipe (21), the bottom baffle (22) is located at the bottom of the material downward flow pipe (21) and the orifice (20), and the heat extraction member (0.3) is fixed on the partition plate (19).

In one preferred embodiment, the bottom baffle (22) is a porous plate or a nonporous plate.

Compared to solutions in the prior art, the advantageous effects of this disclosure include but are not limited to the following aspects:

(1) The dense phase fluidized bed has a relatively high density of bed layer, a relatively low catalyst rate, and a low abrasion.

(2) The gas speed in the material downward flow pipe of the material flow controller is less than or equal to the minimal fluidization speed of the catalyst and the catalyst is in a dense phase packing state, such that a unidirectional dense phase conveying stream of the catalyst is formed, the backmixing of catalyst between adjacent secondary reaction zones (or adjacent secondary regeneration zones) is prevented, and the distribution of residence time is narrow.

(3) The heat extraction member in the material flow controller has an effect of controlling the temperature of the reaction zone.

(4) The reaction zone is separated into n secondary reaction zones by the material flow controller and the catalyst sequentially passes through the $1^{st}$ secondary reaction zone to the $n^{th}$ secondary reaction zone, such that the distribution of residence time is narrow and the uniformity of carbon content of the spent catalyst is greatly increased.

(5) The regeneration zone is separated into m secondary regeneration zones by the material flow controller and the catalyst sequentially passes through the $1^{st}$ secondary regeneration zone to the $m^{th}$ secondary regeneration zone, such that the distribution of residence time is narrow and the uniformity of carbon content of the regenerated catalyst is greatly increased.

(6) Relatively precise control of carbon content of the regenerated catalyst and the spent catalyst is achieved, the distribution of carbon content is relatively uniform, the selectivity for light olefins is increased, and the carbon content may be regulated as needed to optimize the ratio of propylene/ethylene.

(7) Since the distribution of carbon content of the catalyst is relatively uniform, the storage amount of the catalyst required in the reaction zone decreases.

(8) The configuration of a plurality of secondary reaction zones facilitates the achievement of large-scale reactors.

Figure 1:
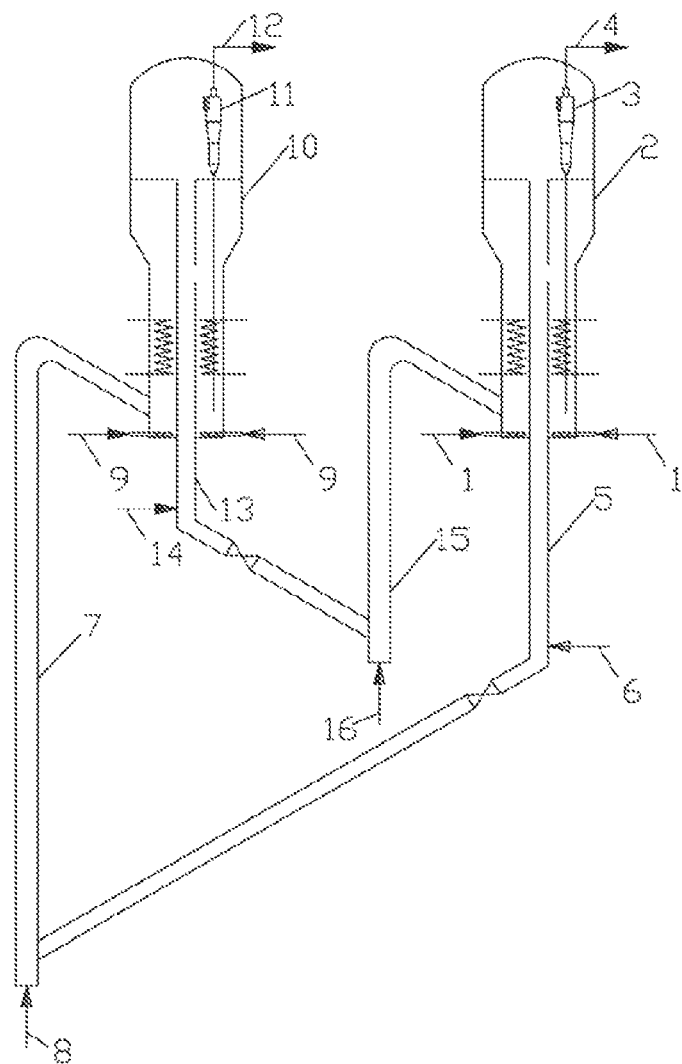
FIG. 1 shows a schematic flow chart of the method in this disclosure.

Reference numerals in the accompanying drawings are described as follows:

1—feeding line for reactor; 1-1 $1^{st}$ secondary reaction zone feed branch line; 1-2 $2^{nd}$ secondary reaction zone feed branch line; 1-3 $3^{rd}$ secondary reaction zone feed branch line; 1-4 $4^{th}$ secondary reaction zone feed branch line; 2—dense phase fluidized bed reactor; 2-1 $1^{st}$ secondary reaction zone; 2-2 $2^{nd}$ secondary reaction zone; 2-3 $3^{rd}$ secondary reaction zone; 2-4 $4^{th}$ secondary reaction zone; 3—cyclone separator; 4—product material line; 5—stripper; 6—water vapor line; 7—lift pipe; 8—lift gas line; 9—feeding line for regenerator; 9-1 $1^{st}$ secondary regeneration zone feed branch line; 9-2 $2^{nd}$ secondary regeneration zone feed branch line; 9-3 $3^{rd}$ secondary regeneration zone feed branch line; 9-4 $4^{th}$ secondary regeneration zone feed branch line; 10—dense phase fluidized bed regenerator; 10-1 $1^{st}$ secondary regeneration zone; 10-2 $2^{nd}$ secondary regeneration zone; 10-3 $3^{rd}$ secondary regeneration zone; 10-4 $4^{th}$ secondary regeneration zone; 11—cyclone separator; 12—exhaust gas line; 13—stripper; 14—water vapor line; 15—lift pipe; 16—lift gas line; 17—material flow controller; 18—material overflow port; 19—partition plate; 20—orifice; 21—material downward flow pipe; 22—bottom baffle; 23—heat extraction member.

DETAILED DESCRIPTION OF THE INVENTION

In order to increase the selectivity for light olefins in the process of preparing light olefins from oxygen-containing compounds, this disclosure provides a reaction device for preparing light olefins from methanol and/or dimethyl ether, which mainly comprises a dense phase fluidized bed reactor (2), a cyclone separator (3), a stripper (5), a lift pipe (7), a dense phase fluidized bed regenerator (10), a cyclone separator (11), a stripper (13), and a lift pipe (15). A feeding line for reactor (1) is connected to the bottom of the dense phase fluidized bed reactor (2). A part of the stripper (5) is in the dense phase fluidized bed reactor (2), and the remaining part thereof is located below the dense phase fluidized bed reactor (2). The water vapor line (6) is connected to the bottom of the stripper (5). The bottom of the lift pipe (7) is connected to the bottom of the stripper (5). The lift gas line (8) is connected to the bottom of the lift pipe (7). The top of the lift pipe 7 is connected to the dense phase fluidized bed regenerator (10). The feeding line for regenerator (9) is connected to the bottom of the dense phase fluidized bed regenerator (10). A part of the stripper (13) is in the dense phase fluidized bed regenerator (10), and the remaining part thereof is located below the dense phase fluidized bed regenerator (10). The water vapor line (14) is connected to the bottom of the stripper (13). The bottom of the lift pipe (15) is connected to the bottom of the stripper (13). The lift gas line (16) is connected to the bottom of the lift pipe (15). The top of the lift pipe (15) is connected to the dense phase fluidized bed reactor (2). Preferably, the feeding line for reactor (1) comprises n reaction zone feed branch lines (1-1, . . . , 1-n), the dense phase fluidized bed reactor (2) is separated into n secondary reaction zones (2-1, . . . , 2-n) by a material flow controller (17), wherein n≥2 and preferably 8≥n≥3; n reaction zone feed branch lines are connected to n secondary reaction zones, respectively; and the $1^{st}$ to the $n^{th}$ secondary reaction zones are sequentially connected, the top of the lift pipe (15) is connected to the $1^{st}$ secondary reaction zone, the $n^{th}$ secondary reaction zone is connected to a material overflow port (18) on the upper part of the stripper (5), a cyclone separator (3) is provided on the upper part of the dense phase fluidized bed reactor (2), a top outlet of the cyclone separator (3) is connected to a product material line (4), and the bottom of the cyclone separator (3) is connected to the $n^{th}$ secondary reaction zone.

Preferably, the feeding line for regenerator (9) comprises m regeneration zone feed branch lines (9-1, . . . , 9-n), the dense phase fluidized bed regenerator (10) is separated into m secondary regeneration zones (10-1, . . . , 10-n) by the material flow controller (17), wherein m≥2 and preferably 8≥m≥3; m regeneration zone feed branch lines are connected to m secondary regeneration zones, respectively; and the $1^{st}$ to the $m^{th}$ secondary regeneration zones are sequentially connected, the top of the lift pipe (7) is connected to the $1^{st}$ secondary regeneration zone, the $n^{th}$ secondary regeneration zone is connected to a material overflow port (18) on the upper part of the stripper (13), a cyclone separator (11) is provided on the upper part of the dense phase fluidized bed regenerator (10), a top outlet of the cyclone separator (11) is connected to an exhaust gas line (12), and the bottom of the cyclone separator (11) is connected to the in secondary regeneration zone.

Preferably, the material flow controller (17) is composed of a partition plate (19), an orifice (20), a material downward flow pipe (21), a bottom baffle (22), and a heat extraction member (23). The orifice (20) is located below the partition plate (19) and is connected to the bottom of the material downward flow pipe (21), a porous plate or a nonporous plate may be used as the bottom baffle (22), which is located at the bottom of the material downward flow pipe (21) and the orifice (20), and the heat extraction member (23) is fixed on the partition plate (19).

In one preferred embodiment, the schematic flow chart of the process for preparing light olefins from methanol in this disclosure is as shown in FIG. 1. Raw materials, which are mainly methanol and/or dimethyl ether, are passed into the dense phase fluidized bed reactor (2) and are brought into contact with a catalyst to generate a gas phase product stream and a spent catalyst; the gas phase product stream and the entrained spent catalyst are passed into the cyclone separator (3), wherein the gas phase product stream is passed to a subsequent working section of separation via the outlet of the cyclone separator and the entrained spent catalyst is passed into the $n^{th}$ secondary reaction zone via the dipleg of the cyclone separator; the regenerated catalyst is passed into the dense phase fluidized bed reactor 2 via the stripper (13) and the lift pipe (15), and is sequentially passed through the $1^{st}$ to the $n^{th}$ secondary reaction zones to form a spent catalyst after carbon deposition; and the spent catalyst is then passed into the dense phase fluidized bed regenerator (10) via the stripper (5) and the lift pipe (7), and is sequentially passed through the $1^{st}$ to the $m^{th}$ secondary regeneration zones to form a regenerated catalyst after charking. The catalyst is preferably a catalyst comprising SAPO molecular sieve, and is further preferably a catalyst comprising SAPO-34 molecular sieve.

Figure 2:
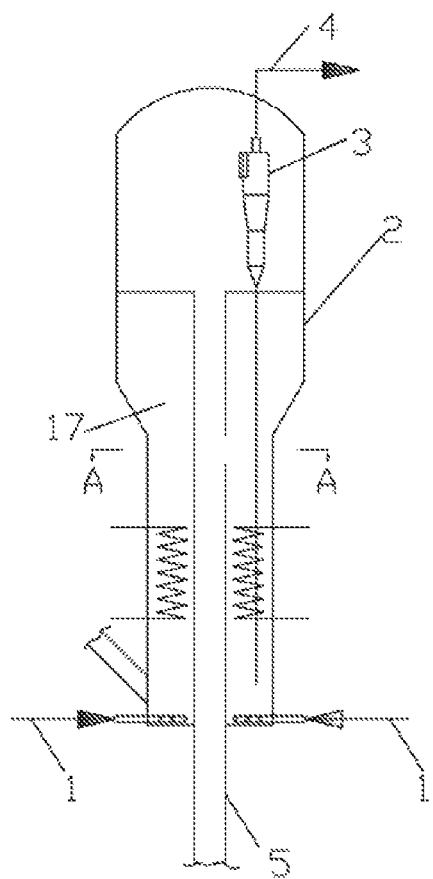
FIG. 2 shows a structural schematic diagram of the dense phase fluidized bed comprising 4 secondary reaction zones in this disclosure, wherein the arrows in A-A sectional view show the flow directions of the catalyst between the secondary reaction zones.
Figure 2:
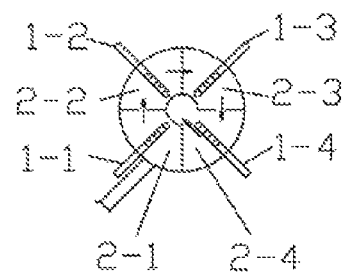

In a specific embodiment, the structural schematic diagram of the dense phase fluidized bed comprising 4 secondary reaction zones in this disclosure is as shown in FIG. 2, wherein the arrows in A-A sectional view show the flow directions of the catalyst between the secondary reaction zones. 3 material flow controllers (17) and a baffle are vertically provided to separate the dense phase fluidized bed reaction zone into 4 secondary reaction zones. The catalyst is sequentially passed through the $1^{st}$ to the $4^{th}$ secondary reaction zones and is then passed into the stripper.

Figure 3:
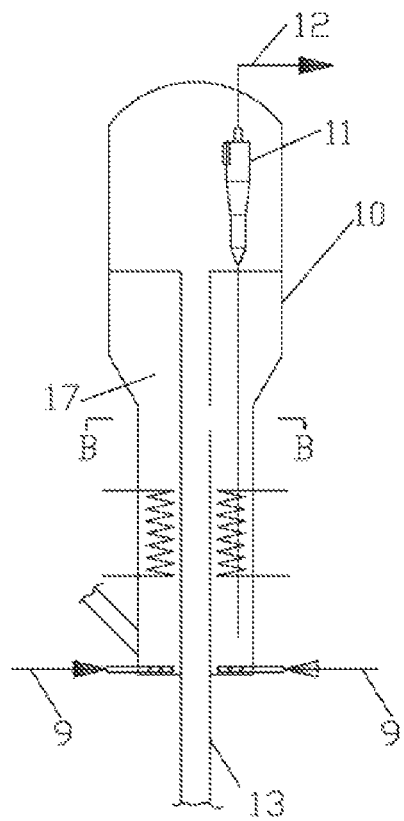
FIG. 3 shows a structural schematic diagram of the dense phase fluidized bed comprising 4 secondary regeneration zones in this disclosure, wherein the arrows in B-B sectional view show the flow directions of the catalyst between the secondary regeneration zones.
Figure 3:
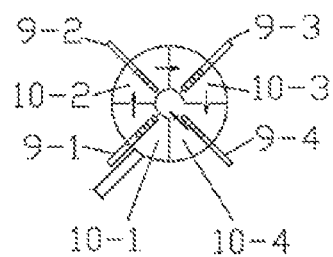

In a specific embodiment, the structural schematic diagram of the dense phase fluidized bed comprising 4 secondary regeneration zones in this disclosure is as shown in FIG. 3, wherein the arrows in B-B sectional view show the flow directions of the catalyst between the secondary regeneration zones. 3 material flow controllers (17) and a baffle are vertically provided to separate the dense phase fluidized bed regeneration zone into 4 secondary regeneration zones. The catalyst is sequentially passed through the $1^{st}$ to the $4^{th}$ secondary regeneration zones and is then passed into the stripper.

Figure 4:
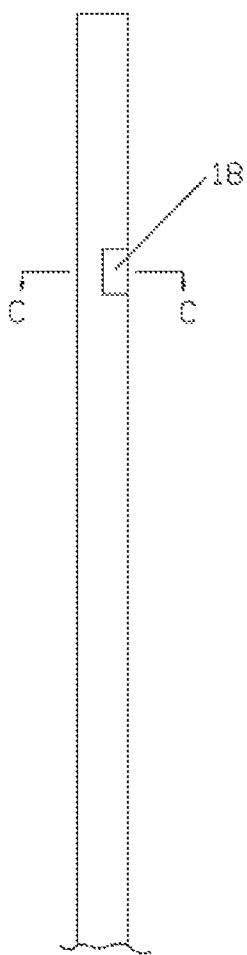
FIG. 4 shows a structural schematic diagram of the stripper in this disclosure.
Figure 4:

Preferably, the structural schematic diagram of the strippers (5 and 13) in this disclosure is as shown in FIG. 4. The opening on the pipe wall on the upper part of the stripper (5) is used as the material overflow port (18) between the $n^{th}$ secondary reaction zone and the stripper (5). The opening on the pipe wall on the upper part of the stripper (13) is used as the material overflow port (18) between the $m^{th}$ secondary regeneration zone and the stripper (13).

Figure 5:
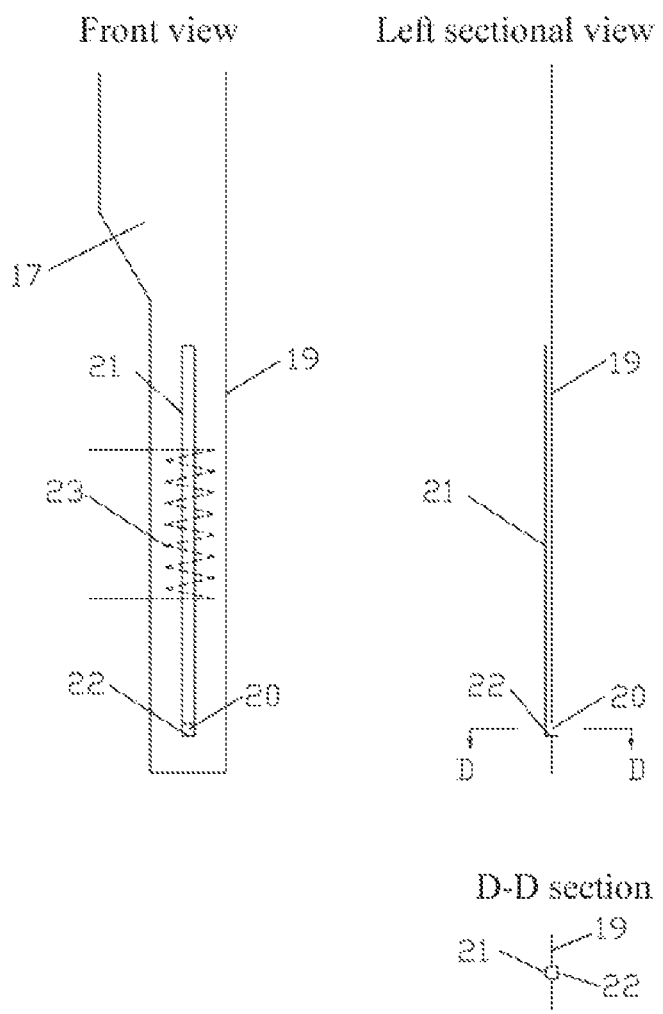
FIG. 5 shows a structural schematic diagram of the material flow controller in this disclosure.

Preferably, the structural schematic diagram of the material flow controller in this disclosure is as shown in FIG. 5. The material flow controller (17) is composed of a partition plate (19), an orifice (20), a material downward flow pipe (21), a bottom baffle (22), and a heat extraction member (23). The catalyst is passed into the material downward flow pipe from the top of the downward flow pipe, wherein the apparent gas linear velocity is less than or equal to the minimal fluidization speed, the catalyst in the material downward flow pipe is in a dense phase packing state, and a material flow driving force is formed to drive the catalyst to flow into a next secondary reaction zones (or regeneration zone) via the orifice. A coil structure may be used as the heat extraction member, which is fixed onto the partition plate.

Preferably, the apparent gas linear velocity in the dense phase fluidized bed reaction zone is 0.1-1.5 m/s; the apparent gas linear velocity in the dense phase fluidized bed regeneration zone is 0.1-1.5 m/s; the apparent gas linear velocity in the material flow controller is less than or equal to the minimal fluidization speed of the catalyst; the catalyst is preferably a catalyst comprising SAPO molecular sieve, and is further preferably a catalyst comprising SAPO-34 molecular sieve; a feed port is provided at the bottom of the reaction zone, and the feed comprises methanol and/or dimethyl ether, etc.; the stripping medium of the stripper (13) comprises water vapor; a regenerating medium inlet is provided at the bottom of the regeneration zone (10), and the regenerating medium comprises air, oxygen-depleted air, water vapor, etc.; the reaction zone (2) has a reaction temperature of 400-550° C. and a bed layer density of 200-1.200 kg/m$^3$, and the average amount of carbon deposition of the catalyst sequentially increases from the $1^{st}$ secondary reaction zone to the $n^{th}$ secondary reaction zone, wherein the average amount of carbon deposition of the $1^{st}$ secondary reaction zone is 0.5-3 wt % and the average amount of carbon deposition of the $n^{th}$ secondary reaction zone is 7-10 wt %; and the regeneration zone (10) has a reaction temperature of 500-700° C. and a bed layer density of 200-1200 kg/m$^3$, and the average amount of carbon deposition of the catalyst sequentially decreases from the $1^{st}$ secondary regeneration zone to the $m^{th}$ secondary regeneration zone, wherein the average amount of carbon deposition of the $1^{st}$ secondary regeneration zone is 3-10 wt % and the average amount of carbon deposition of the $m^{th}$ secondary regeneration zone is 0-3 wt %. The object of controlling the amount of carbon deposition on catalyst, improving the uniformity of carbon content, and increasing the selectivity of light olefins can be achieved by using the method of this disclosure, which has relatively high technical advantages and can be used in the industrial production of light olefins.

In order to heifer illustrate this disclosure and facilitate the understanding of the technical solution of this disclosure, typical and non-limiting Examples of this disclosure are as follows.

Example 1

4 secondary reaction zones were provided in the dense phase fluidized bed reactor, and 4 secondary regeneration zones were provided in the dense phase fluidized bed regenerator. Raw materials, which were mainly methanol and/or dimethyl ether, were passed into the dense phase fluidized bed reactor and were brought into contact with a catalyst comprising SAPO-34 molecular sieve to generate a gas phase product stream and a spent catalyst. The gas phase material and the entrained spent catalyst were passed into the cyclone separator, wherein the gas phase product stream was passed to a subsequent working section of separation via the outlet of the cyclone separator and the entrained spent catalyst was passed into the $4^{th}$ secondary reaction zone via the di Dog of the cyclone separator. The regenerated catalyst was passed into the dense phase fluidized bed reactor via the stripper and the lift pipe, and was sequentially passed through the $1^{st}$ to the $4^{th}$ secondary reaction zones to form a spent catalyst after carbon deposition. The spent catalyst was then passed into the dense phase fluidized bed regenerator via the stripper and the lift pipe, and was sequentially passed through the $1^{st}$ to the $4^{th}$ secondary regeneration zones to forma regenerated catalyst after charking. The reaction conditions of the dense phase fluidized bed reactor were as follows: the reaction temperature was 400° C., the gas phase linear velocity was 0.3 m/s, the bed layer density was 1000 kg/m$^3$, the average amount of carbon deposition of the $1^{st}$ secondary reaction zone was 2 wt %, the average amount of carbon deposition of the $2^{nd}$ secondary reaction zone was 6 wt %, the average amount of carbon deposition of the $3^{rd}$ secondary reaction zone was 8 wt %, and the average amount of carbon deposition of the $4^{th}$ secondary reaction zone was 10 wt %. The reaction conditions of the dense phase fluidized bed regenerator were as follows: the reaction temperature was 500° C., the gas phase linear velocity was 0.3 m/s, the bed layer density was 1000 kg/m$^3$, the average amount of carbon deposition of the $1^{st}$ secondary regeneration zone was 7 wt %, the average amount of carbon deposition of the $2^{nd}$ secondary regeneration zone was 4 wt %, the average amount of carbon deposition of the $3^{rd}$ secondary regeneration zone was 2 wt %, and the average amount of carbon deposition of the $4^{th}$ secondary regeneration zone was 1 wt %. The reaction product was analyzed by online gas chromatography, and the carbon based yield of light olefins was 91.1 wt %.

Example 2

3 secondary reaction zones were provided in the dense phase fluidized bed reactor, and 2 secondary regeneration zones were provided in the dense phase fluidized bed regenerator. Raw materials, which were mainly methanol and/or dimethyl ether, were passed into the dense phase fluidized bed reactor and were brought into contact with a catalyst comprising SAPO-34 molecular sieve to generate a gas phase product stream and a spent catalyst. The gas phase material and the entrained spent catalyst were passed into the cyclone separator, wherein the gas phase product stream was passed to a subsequent working section of separation via the outlet of the cyclone separator and the entrained spent catalyst was passed into the $3^{rd}$ secondary reaction zone via the dipleg of the cyclone separator. The regenerated catalyst was passed into the dense phase fluidized bed reactor via the stripper and the lift pipe, and was sequentially passed through the $1^{st}$ to the $3^{rd}$ secondary reaction zones to form a spent catalyst after carbon deposition. The spent catalyst was then passed into the dense phase fluidized bed regenerator via the stripper and the lift pipe, and was sequentially passed through the $1^{st}$ to the $2^{nd}$ secondary regeneration zones to form a regenerated catalyst after charking. The reaction conditions of the dense phase fluidized bed reactor were as follows: the reaction temperature was 450° C., the gas phase linear velocity was 0.5 m/s, the bed layer density was 900 kg/m$^3$, the average amount of carbon deposition of the $1^{st}$ secondary reaction zone was 3 wt %, the average amount of carbon deposition of the $2^{nd}$ secondary reaction zone was 7 wt %, and the average amount of carbon deposition of the $3^{rd}$ secondary reaction zone was 9 wt %. The reaction conditions of the dense phase fluidized bed regenerator were as follows: the reaction temperature was 600° C., the gas phase linear velocity was 0.7 m/s, the bed layer density was 700 kg/m$^3$, the average amount of carbon deposition of the $1^{st}$ secondary regeneration zone was 4 wt %, and the average amount of carbon deposition of the $2^{nd}$ secondary regeneration zone was 2 wt %. The reaction product was analyzed by online gas chromatography, and the carbon based yield of light olefins was 90.5 wt %.

Example 3

6 secondary reaction zones were provided in the dense phase fluidized bed reactor, and 5 secondary regeneration zones were provided in the dense phase fluidized bed regenerator. Raw materials, which were mainly methanol and/or dimethyl ether, were passed into the dense phase fluidized bed reactor and were brought into contact with a catalyst comprising SAPO-34 molecular sieve to generate a gas phase product stream and a spent catalyst. The gas phase material and the entrained spent catalyst were passed into the cyclone separator, wherein the gas phase product stream was passed to a subsequent working section of separation via the outlet of the cyclone separator and the entrained spent catalyst was passed into the $6^{th}$ secondary reaction zone via the dipleg of the cyclone separator. The regenerated catalyst was passed into the dense phase fluidized bed reactor via the stripper and the lift pipe, and was sequentially passed through the $1^{st}$ to the $6^{th}$ secondary reaction zones to form a spent catalyst after carbon deposition. The spent catalyst was then passed into the dense phase fluidized bed regenerator via the stripper and the lift pipe, and was sequentially passed through the $1^{st}$ to the $5^{th}$ secondary regeneration zones to form a regenerated catalyst after charking. The reaction conditions of the dense phase fluidized bed reactor were as follows: the reaction temperature was 480° C., the gas phase linear velocity was 0.7 m/s, the bed layer density was 700 kg/m$^3$, the average amount of carbon deposition of the $1^{st}$ secondary reaction zone was 1 wt %, the average amount of carbon deposition of the $2^{nd}$ secondary reaction zone was 3 wt %, the average amount of carbon deposition of the $3^{rd}$ secondary reaction zone was 4 wt %, the average amount of carbon deposition of the $4^{th}$ secondary reaction zone was 5 wt %, the average amount of carbon deposition of the $5^{th}$ secondary reaction zone was 6 wt %, and the average amount of carbon deposition of the $6^{th}$ secondary reaction zone was 7 wt %. The reaction conditions of the dense phase fluidized bed regenerator were as follows: the reaction temperature was 650° C., the gas phase linear velocity was 1.0 m/s, the bed layer density was 500 kg/m$^3$, the average amount of carbon deposition of the $1^{st}$ secondary regeneration zone was 5 wt %, the average amount of carbon deposition of the $2^{nd}$ secondary regeneration zone was 3 wt %, the average amount of carbon deposition of the $3^{rd}$ secondary regeneration zone was 2 wt %, the average amount of carbon deposition of the $4^{th}$ secondary regeneration zone was 1 wt %, and the average amount of carbon deposition of the $5^{th}$ secondary regeneration zone was 0.01 wt %. The reaction product was analyzed by online gas chromatography, and the carbon based yield of light olefins was 91.4 wt %.

This disclosure has been described in detail above, but this disclosure is not limited to specific embodiments described herein. It is to be understood by the person skilled in the art that other modifications and variations can be made without departing from the scope of the disclosure. The scope of the disclosure is defined by the appended claims.

What is claimed is:

1. A reaction device for preparing light olefins from methanol and/or dimethyl ether comprising a dense phase fluidized bed reactor, a cyclone separator, a stripper, a lift pipe, a dense phase fluidized bed regenerator, a cyclone separator, a stripper, and a lift pipe; wherein a feeding line for reactor is connected to the bottom of the dense phase fluidized bed reactor; a part of the stripper is in the dense phase fluidized bed reactor, and the remaining part thereof is below the dense phase fluidized bed reactor; the bottom of the lift pipe is connected to the bottom of the stripper, and the top of the lift pipe is connected to the dense phase fluidized bed regenerator; a feeding line for regenerator is connected to the bottom of the dense phase fluidized bed regenerator; a part of the stripper is in the dense phase fluidized bed regenerator, and the remaining part thereof is below the dense phase fluidized bed regenerator; the bottom of the lift pipe is connected to the bottom of the stripper, and the top of the lift pipe is connected to the dense phase fluidized bed reactor, wherein a material flow controller is provided in the dense phase fluidized bed reactor and/or the dense phase fluidized bed regenerator, and the dense phase fluidized bed reactor is separated into n secondary reaction zones by the material flow controller and the $1^{st}$ to the $n^{th}$ secondary reaction zones are sequentially connected; the dense phase fluidized bed regenerator is separated into m secondary regeneration zones by the material flow controller and the $1^{st}$ to the $m^{th}$ secondary regeneration zones are sequentially connected; and wherein n≥2, and m≥2.

2. The reaction device according to claim 1, wherein the top of the lift pipe is connected to the $1^{st}$ secondary reaction zone, the $n^{th}$ secondary reaction zone is connected to a material overflow port on the upper part of the stripper; and the cyclone separator is provided on the upper part of the dense phase fluidized bed reactor, a top outlet of the cyclone separator is connected to a product material line, and the bottom of the cyclone separator is connected to the $n^{th}$ secondary reaction zone.

3. The reaction device according to claim 2, wherein the material flow controller is composed of a partition plate, an orifice, a material downward flow pipe, a bottom baffle, and a heat extraction member; and the orifice is located below the partition plate and is connected to the bottom of the material downward flow pipe, the bottom baffle is located at the bottom of the material downward flow pipe and the orifice, and the heat extraction member is fixed on the partition plate.

4. The reaction device according to claim 3, wherein the bottom baffle is a porous plate or a nonporous plate.

5. The reaction device according to claim 1, wherein top of the lift pipe is connected to the $1^{st}$ secondary regeneration zone, the $m^{th}$ secondary regeneration zone is connected to a material overflow port on the upper part of the stripper; and the cyclone separator is provided on the upper part of the dense phase fluidized bed regenerator, a top outlet of the cyclone separator is connected to an exhaust gas line, and the bottom of the cyclone separator is connected to the $m^{th}$ secondary regeneration zone.

6. The reaction device according to claim 5, wherein the material flow controller is composed of a partition plate, an orifice, a material downward flow pipe, a bottom baffle, and a heat extraction member; and the orifice is located below the partition plate and is connected to the bottom of the material downward flow pipe, the bottom baffle is located at the bottom of the material downward flow pipe and the orifice, and the heat extraction member is fixed on the partition plate.

7. The reaction device according to claim 6, wherein the bottom baffle is a porous plate or a nonporous plate.

8. The reaction device according to claim 1, wherein 8≥n≥3.

9. The reaction device according to claim 8, wherein the material flow controller is composed of a partition plate, an orifice, a material downward flow pipe, a bottom baffle, and a heat extraction member; and the orifice is located below the partition plate and is connected to the bottom of the material downward flow pipe, the bottom baffle is located at the bottom of the material downward flow pipe and the orifice, and the heat extraction member is fixed on the partition plate.

10. The reaction device according to claim 9, wherein the bottom baffle is a porous plate or a nonporous plate.

11. The reaction device according to claim 1, wherein 8≥m≥3.

12. The reaction device according to claim 11, wherein the material flow controller is composed of a partition plate, an orifice, a material downward flow pipe, a bottom baffle, and a heat extraction member; and the orifice is located below the partition plate and is connected to the bottom of the material downward flow pipe, the bottom baffle is located at the bottom of the material downward flow pipe and the orifice, and the heat extraction member is fixed on the partition plate.

13. The reaction device according to claim 1, wherein the material flow controller is composed of a partition plate, an orifice, a material downward flow pipe, a bottom baffle, and a heat extraction member; and the orifice is located below the partition plate and is connected to the bottom of the material downward flow pipe, the bottom baffle is located at the bottom of the material downward flow pipe and the orifice, and the heat extraction member is fixed on the partition plate.

14. The reaction device according to claim 13, wherein the bottom baffle is a porous plate or a nonporous plate.

15. The reaction device according to claim 14, wherein the bottom baffle is a porous plate or a nonporous plate.

* * * * *